United States Patent [19]

Radmer

[11] Patent Number: 4,952,511
[45] Date of Patent: Aug. 28, 1990

[54] PHOTOBIOREACTOR

[75] Inventor: Richard J. Radmer, Catonsville, Md.

[73] Assignee: Martek Corporation, Columbia, Md.

[21] Appl. No.: 338,532

[22] Filed: Apr. 14, 1989

Related U.S. Application Data

[63] Continuation of Ser. No. 60,609, Jun. 11, 1987, abandoned.

[51] Int. Cl.$^5$ .............................................. C12M 1/08
[52] U.S. Cl. .................................... 435/314; 435/287; 362/805; 362/32; 362/340; 47/1.4
[58] Field of Search ............... 435/257, 287, 313, 314; 362/340, 805, 32; 47/1.4; 126/439, 440

[56] References Cited

U.S. PATENT DOCUMENTS

| | | | |
|---|---|---|---|
| 823,620 | 6/1906 | Mygatt | 362/340 |
| 1,762,383 | 6/1930 | Booraem | 362/32 |
| 2,225,151 | 12/1940 | Borba | 362/102 |
| 2,642,519 | 6/1953 | Caustin et al. | 362/32 |
| 2,815,607 | 12/1957 | Schroeder | 435/313 X |
| 3,986,297 | 10/1976 | Ichimura et al. | 47/1.4 |
| 4,260,220 | 4/1981 | Whitehead | 350/102 X |
| 4,422,719 | 12/1983 | Orcutt | 362/32 X |

FOREIGN PATENT DOCUMENTS

| | | | |
|---|---|---|---|
| 0084325 | 7/1983 | European Pat. Off. | 435/257 |
| 0103729 | 3/1984 | European Pat. Off. | 362/32 |
| 611716 | 10/1926 | France | 362/340 |
| 0132170 | 11/1978 | Japan | 47/1.4 |
| 0057041 | 12/1985 | Japan | 435/257 |

OTHER PUBLICATIONS

Radmer et al., Biotech Y Bioeng. 29, (1987).
Mori et al., Adv. in Space Res. 1986 (McElroy & Shoog, Eds.) Pergammon Press (1987).
Mori et al., Expert, Aug. 1983, pp. 94–99.
Lee, Y. K. Tibtech, Jul. 1986, pp. 186–189.
Products & Services Manual by TIR Systems Ltd., Jul. 1, 1985.

*Primary Examiner*—Carl D. Price
*Attorney, Agent, or Firm*—Bernard, Rothwell & Brown

[57] ABSTRACT

A photobioreactor for the cultivation of photosynthetic microorganisms comprises a tank, one or more light compartments extending into the tank and one or more high intensity lamps whose light is directed into the light compartments. Each light compartment has at least one transparent wall and a means for distributing light from the lamp substantially uniformly across the transparent wall.

12 Claims, 3 Drawing Sheets

PHOTOBIOREACTOR

BACKGROUND OF THE INVENTION

Algae have been cultivated artificially for such diverse purposes as the production of food for animals and humans, the treatment of sewage and waste waters, and the accumulation of radioactive wastes. More recently, algal cultures have been used for the production of enzymes having industrial and research applications and for producing oils and other materials having nutritional value. Modern biotechnology offers an opportunity for the genetic modification of algae to yield cultures capable of producing a wide variety of useful materials.

Various methods and equipment have been employed for the artificial culturing of algae. Perhaps the simplest procedures have involved the use of shallow open ponds exposed to sunlight. Such ponds are subject to contamination by dust, other microorganisms, insects and environmental pollutants and provide minimal ability to control the degree of exposure to light, temperature, respiration and other important factors. A more sophisticated approach has involved growing algal cultures in plastic-covered trenches and ponds, optionally having electrically powered pumps and agitators. These configurations reduce the chances of contamination of the culture and permit more accurate control of temperature, respiration and other parameters. Such configurations are still quite inefficient in terms of providing adequate and uniform amounts of light to the algal cells, particularly when sunlight is the sole source of light.

Unlike other microorganisms, the nutrient requirements of algae are very inexpensive carbon dioxide being the principal source of carbon. On the other hand, the photosynthetic processes require that the algae be exposed to a relatively constant and uniform source of light. A primary design factor for modern photobioreactors involves providing a means for uniformly exposing the cells in the algal culture to the optimum amount of visible light. Like many plants, algae are quite sensitive to the amount and kind of light. Excessive light intensity can damage and kill algal cells. Too little light results in low levels of photosynthesis.

A number of design factors are affected by the means selected for supplying light to the cells. For example, light sources, including natural sunlight, often emit substantial amounts of heat. Algal cultures are sensitive to heat, and many of them grow most efficiently at relatively low temperatures (e.g., about 27° C). Thus, means must often be provided for cooling the algal culture and dissipating heat generated by the light source.

Two design factors closely related to the requirement for a uniform and constant supply of light are the cell density and the light path length. Like conventional fermentation processes, it is usually desirable to use as high a cell density as possible. Many of the same considerations apply to algal cultures as to bacterial cultures. For example, in addition to the light requirements, one must take into account the competition for nutrients, respiratory demands, viscosity and pumpability of the culture medium, and the like. An extremely high cell density results in cells more than a few millimeters from the light source being effectively shielded from the light. Simply increasing light intensity will not overcome this problem, because highly intense light will damage or kill cells near the light source.

The only effective way of increasing cell densities while maintaining a uniform amount of light is to employ a relatively short light path length. Of course, the requirement that the photobioreactor have a relatively short light path length introduces a new set of design problems. For industrial applications, it is usually desirable to employ high-volume microbial cultures. Large culture volumes are amenable to continuous or large-scale batch recovery operations and generally result in economies of scale. Satisfying the requirements for large culture volumes and short light path lengths mandates that the photobioreactor have large, transparent walls which are closely spaced to define a light path and a fluid chamber within which the algal culture is contained. The transparent walls are illuminated with an appropriate light source to sustain the growth and photosynthetic reactions of the cells.

Various designs of such photobioreactors have been employed A relatively simple design which has been successfully used in laboratory and pilot plant operations is simply a glass chamber having large, flat, parallel side walls and a narrow bottom and end walls. A gas sparging tube is placed in the bottom of the chamber to allow carbon dioxide or carbon dioxide-enriched air to be sparged through a culture medium contained in the chamber, and banks of fluorescent light tubes are arranged adjacent to the side walls of the chamber. Inocula, nutrients, buffers, and the like can be introduced into the chamber through the top which may optionally be covered with a lid. This design has been very successful and useful for small scale operations, but scale-up to industrial operations poses numerous difficulties. A primary difficulty is safety-related. The fluorescent lighting must be arranged uniformly along the side walls of the chambers. As greater numbers of chambers are used, the presence of a large number of fluorescent tubes and the accompanying electrical circuitry poses a substantial risks of electrical shorting and electrocution of operators resulting from rupture or breakage of a chamber.

In addition, large banks of fluorescent tubes and their accompanying sockets, mounting brackets, electrical circuitry and the like are quite expensive from both the standpoint of initial capital investment and continuous power requirements. In particular, such designs involve large installation and maintenance costs.

An alternative embodiment of a bioreactor employing a fluorescent tube involves a cylindrical culture chamber having glass walls which surround a single fluorescent tube. The culture chamber may also be surrounded by a concentric cylindrical water jacket for controlling the temperature of the culture. Such a photobioreactor is described by Radmer, R., Behrens, P., and Arnett, L., "An Analysis of the Productivity of a Continuous Algal Culture System," *Biotechnology and Bioengineering*, 29 pp. 488–4392 (1987). This design has also proven very valuable for laboratory-scale algal culturing operate ions, but, for many of the reasons described above, has not proven particularly useful for large-scale operations.

Thus, in recent attempts to design large-scale photobioreactors, attention has been focused on devising efficient means for distributing light uniformly, and in the correct intensity, across large transparent walls of the reactor. One approach to this problem has been to use fiber optic cables to distribute light from one or more high-intensity light sources to an algal culture medium. This approach is described, for example, by Mori, K., Ohya, H., and Furune, H., "Sunlight Supply System and Gas Exchange in Microalgal Bioreactor System." *Advances in Space Research* 1986. Eds. R.D. McElroy and A.I. Shoog, Pergammon Press (1987) (in press). A principal disadvantage of using fiber optic cables for large-scale photobioreactors is their cost. To provide a uniform distribution of light over large surface areas, a very large number of optical fibers must be employed. Both the capital investment and the fabrication costs associated with such a system can be prohibitive.

Various photobioreactor designs are reviewed in an article by Yuan-Kun Lee, "Enclosed Bioreactors for the Mass Cultivation of Photosynthetic Microorganisms: The Future Trend," *TIBTECH*, July 1986, p. 186-189. A significant need still exists for large-scale photobioreactors capable of using high intensity, low-cost lamps which are physically remote from and preferably above the liquid culture medium to minimize electrical hazards and transfer of heat from the lamps to the culture medium.

SUMMARY OF THE INVENTION

In accordance with the present invention, a novel photobioreactor comprises:
(a) a tank for containing a liquid microbial culture;
(b) a high-intensity light source whose light is substantially entirely directed into a water-tight light compartment;
(c) said light compartment having at least one transparent wall extending into said tank; and
(d) means for substantially uniformly distributing light from said high-intensity light source across the interior surface of said transparent wall.

The photobioreactor of this invention can employ high-intensity point sources of light rather than fluorescent tubes, and the lamps and associated electrical circuitry can be physically remote from the liquid culture medium. The photobioreactor can employ lamps having higher efficiencies and intensities than conventional fluorescent tubes, which results in lower capital costs as well as lower operating costs, especially installation and maintenance labor costs.

Detailed Description of the Invention

Figure 1:
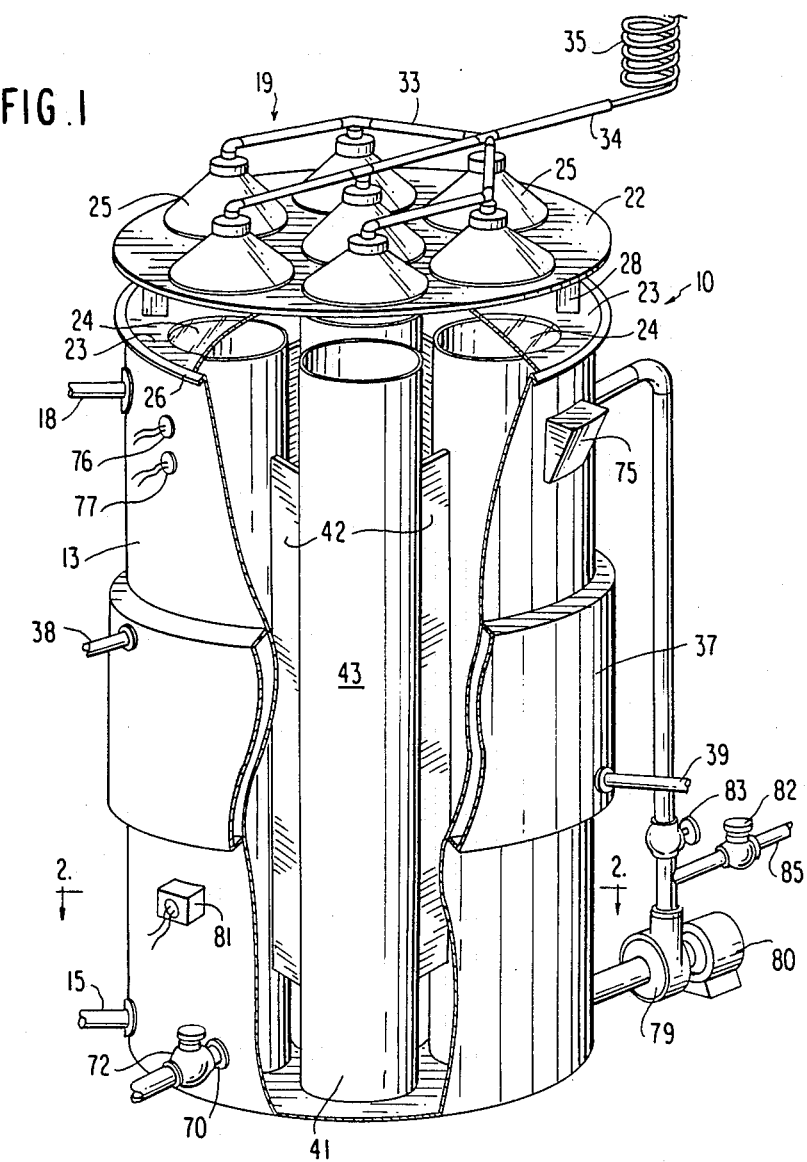
FIG. 1 is a perspective view in partial section of one embodiment of a photobioreactor in accordance with the present invention.

A preferred embodiment of the photobioreactor of this invention is shown in FIGS. 1-4. Referring to FIG. 1, photobioreactor 10 comprises a tank 13 for containing a liquid culture medium. The liquid culture medium is sometimes referred to herein as an "algal" culture, but it will be appreciated that the photobioreactor may be employed for the cultivation of any type of photosynthetic microorganism.

Tank 13 may be of any convenient shape, and it is preferably substantially cylindrical. Tank 13 may be constructed of a variety of materials, such as stainless steel, various plastic materials, glass and the like. Because of its strength and relative inertness, stainless steel is a preferred construction material.

Tank 13 is covered by lid 23. Lid 23 is preferably constructed of stainless steel and contains windows 24 made of a heat resistant transparent material, such as tempered glass. Windows 24 are configured so as to permit light to be directed into tank 13 as hereinafter described. Alternatively, lid 23 may be constructed entirely of a heat resistant transparent material. The top rim of tank 13 may be formed into a lip 26 which permits lid 23 to be bolted or clamped to the top of tank 13. In addition, the top rim of tank 13 may be fitted with a gasket material (not shown) to provide a liquid and gas-tight seal with lid 23.

Figure 3:
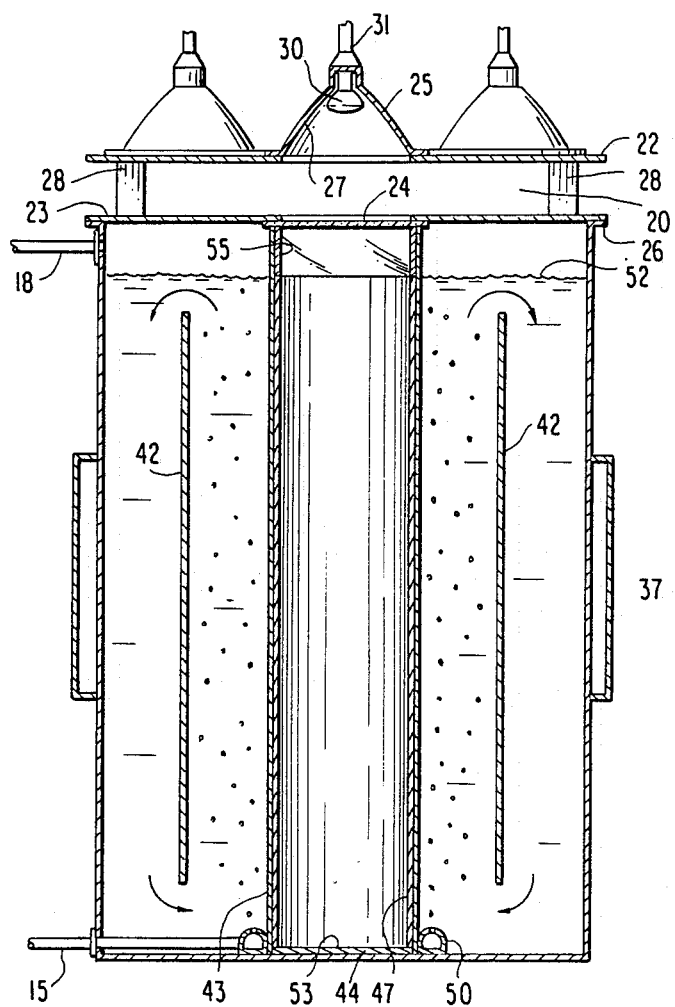
FIG. 3 is a longitudinal sectional view taken along line 3—3 of FIG. 2.

Suspended above lid 23 is a light assembly 19 which comprises one or more lamps 25 for directing light through windows 24 into tank 13. Lamp assembly 19 consists of plate 22 upon which is mounted one or more lamps 25. As best shown in FIG. 3, lamp 25 consists of a light source 30, a reflector 27 and associated electrical connections 31. Light source 30 advantageously is a high-efficiency, high-intensity light source which emits light primarily in the visible portion of the spectrum. A wide variety of light sources may be used, and a particularly preferred light source is the well-known sodium vapor lamp, whose emission spectrum is well-suited to the light requirements of most algae. Sodium vapor lamps are produced in mass quantities, because they are widely used for nighttime illumination of streets and buildings; therefore, they are relatively inexpensive. They are also efficient from an operating standpoint and produce a highly intense light. Other high intensity light sources may be employed, including mercury vapor lamps, arc lamps, xenon lamps, and the like. Plate 22 has an opening associated with each lamp 25, which conforms substantially in shape and size with the outer flange of reflector 27, thus permitting substantially all of the light emitted by light source 30 to be directed downwardly through the opening in plate 22 and the windows 24 in lid 23. Reflector 27 focuses the light emitted by light source 30 through windows 24, and also results in some divergence of the light rays as they pass through window 24. The wiring which supplies electrical current to light source 30 passes through conduits 33 to each of the lamps 25. Conduits 33 are hermetically sealed to lamps 25 and are substantially water-tight, thus minimizing the chances of electrical shorting or electrocution resulting from the damp environment surrounding the photobiorector 10. As shown in FIG. 1, conduits 33 converge into a single outlet conduit 34, and power cord 35, which is the main source of power, is in the form of a resilient coil to permit light assembly 19 to be raised for cleaning or maintenance without disconnecting the electrical supply.

Tank 13 contains a plurality of light compartments 41. Light compartment 41 comprise transparent walls 43 which may be constructed of glass or transparent plastic sheet material. In a preferred embodiment, light compartments 41 are substantially cylindrical and the axes of adjacent light compartments are substantially parallel to one another and are substantially perpendicular to lid 23. Walls 43 extend substantially the entire length of tank 13, thus a major portion of light compartment 41 is submerged in a liquid algal culture medium contained in tank 13.

Figure 2:
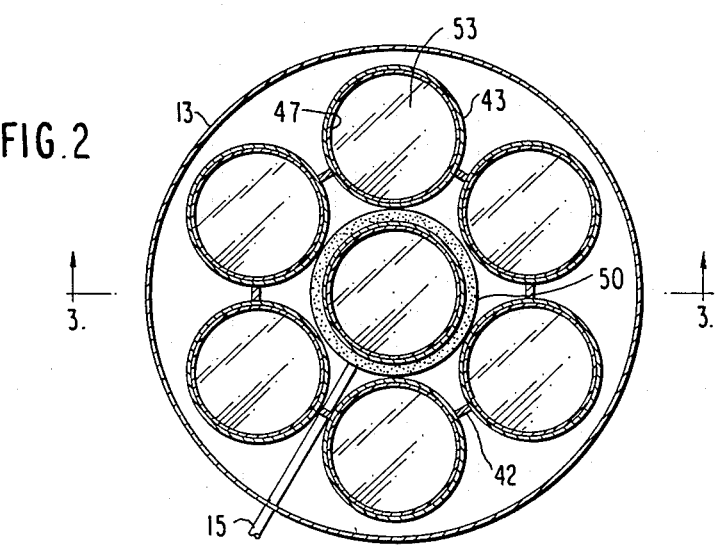
FIG. 2 is a sectional view taken along line 2—2 of FIG. 1.

As best shown in FIG. 2, light compartments 41 are preferably distributed uniformly throughout tank 13 in a geometric pattern. In a particularly preferred pattern, the axes of any three adjacent light compartments forms an equilateral triangle. The photobioreactors may be conveniently produced in different sizes, wherein the number of light compartments contained in tank 13 is 1, 7, 19, 37, 61, 91, etc., according to the formula $$N = 6 \sum_{o}^{n} x + 1$$

wherein N is the number of light compartments and n is the number of concentric rings of light compartments around the center of tank 13 (counting the center light compartment as the zero ring) and x is an integer. Walls 43 of adjacent light compartments 41 cooperate to form a light path which can contain a liquid algal culture medium. The spacing between walls 43 of adjacent light compartments 41 is designed such that a photosynthesis-supporting amount of light is transmitted through transparent walls 43 and substantially throughout said light path. Accordingly, cells contained in the light path are exposed to a uniform light of an appropriate intensity and wavelength for supporting growth and photosynthetic reactions. The surface areas of walls 43 and the intensity of light source 30 preferably are selected to provide a light intensity in the visible region of the spectrum (400nm–700nm) across the inner surfaces of walls 43 of from about 10 to about 100 watts of light per square meter, preferably from about 20 to about 60 watts per square meter.

The optimum dimensions of the light paths formed by walls 43 of adjacent light compartments 41 will vary depending upon the type of culture used and the cell density. A particular advantage of the photobioreactors of this invention is that, by increasing the number of lamps and light compartments, large-volume reactors having relatively short light paths can be constructed. Such short light paths permit the use of relatively high cell densities, thus maximizing bioconversion efficiencies and cell product yields. In general, the light paths will range from about 0.5 to about 50 centimeters. The longer light paths (e.g., from about 30 cm to 50 cm) may be particularly suited to the cultivation of photoheterotrophic algae and bacteria, whose light requirements are significantly lower than those of many algal species. For photoautotrophic algal cultures, the light paths preferably range from about 1.5 to about 3 centimeters. For cylindrical light compartments, the light path is defined as the intersticial distance between the points at which the outer surfaces of walls 43 of adjacent light compartments are intersected by a transverse line connecting the axes of such light compartments. For light compartments having a different shape or arrangement within the photobioreactor, the light path is defined as the average distance between the walls of adjacent light compartments.

Plate 22 carrying lamps 25 is preferably separated from lid 23 by a small air space, as shown in FIG. 1. The size of the air space is large enough to provide ventilation between lamps 25 and transparent windows 24 to assist in the dissipation of heat, but is not so large as to cause excessive losses of light. Transparent windows 24 are advantageously constructed of a heat resistant transparent material, such as tempered glass, to prevent damage resulting from heat generated by light sources 30. The spacing between plate 22 and lid 23 may be maintained conveniently by legs 28 attached either to the bottom of plate 22 or the top of lid 23. The arrangement of lamps 25 in plate 22 and windows 24 in lid 23 is substantially the same as the arrangement of light compartments 41 in tank 13. Thus, light from light sources 30 is reflected by reflectors 27 through the openings in plate 22 and windows 24 into light compartments 41.

Cooling means may be provided to control the temperature of an algal culture contained in tank 13. Such cooling means may be in the form of a cooling jacket 37 surrounding a portion of the wall of tank 13. Such cooling jacket provides a means for circulating cooling water or other fluid across the wall of tank 13 to absorb heat and assist in controlling the temperature of an algal medium contained in tank 13. Cooling water enters jacket 37 through inlet tube 39 and exits through exit tube 38. The dimensions of cooling jacket 37 will depend upon a number of factors, such as the amount of heat transmitted by light sources 30 to the liquid culture medium contained in tank 13, the desired temperature of the culture medium, the temperature and flow rate of the cooling water, and the like. In general, it has been found that a cooling jacket covering a surface area of about one square foot for each twenty liters of volume of tank 13 is adequate.

The portion of each light compartment 41 which will be submerged in a liquid culture medium is water-tight. Referring to FIG. 3, a bottom 44 is sealed to the lower rim of wall 43 of each light compartment 41, thus forming a water-tight seal. The top rim of wall 43 extends above the liquid level 52 of an algal culture medium contained within tank 13. Preferably, the top rim of wall 43 is sealed to the bottom of window 24, thus preventing water vapor from entering light compartment 41.

Light compartment 41 contains means for substantially uniformly distributing light from light source 30 and reflector 27 across the interior surface of transparent wall 33. Such means may be in the form of a light guide constructed of internally reflective prismatic sheet material. Such internally reflective prismatic sheet material is formed from a highly transparent flexible plastic sheet, such as polyacrylate, one surface of which is inscribed with minute 90° corrugations. As a result of these corrugations, light striking the sheet with an angle of incidence of about 27° or less is reflected with nearly 100% efficiency. When these reflective sheets are formed into hollow tubes, they serve as highly efficient light guides. Minor imperfections in the prismatic sheets as well as light rays impinging the sheets at angles greater than about 27° result in the transmission of light through the prismatic sheet material. The prismatic sheet material and light guides formed therefrom are described by Lorne A. Whitehead in U.S. Pat. No. 4,260,220, incorporated herein by reference.

Figure 4:
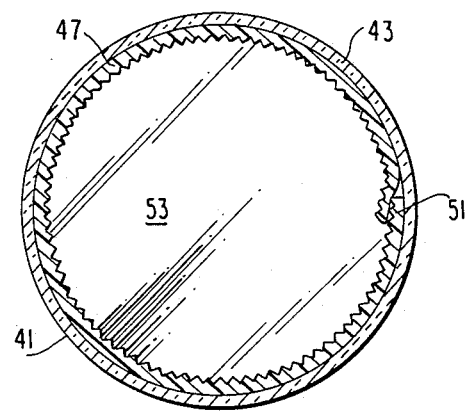
FIG. 4 is an enlarged cross-section of one of the light compartments of the photobioreactor of FIG. 1 taken along lines 2—2 of FIG. 1.

An enlarged cross section of light compartment 41 is shown in FIG. 4. A cylinder 47 of prismatic sheet material is disposed inside of light compartment 41. The thickness of the prismatic sheet material and the corrugations on its inner surface are exaggerated in FIG. 4 for illustration. The prismatic sheet material conveniently may be rolled into a cylinder which is placed inside of light compartment 41 and expanded to line the inner surface of wall 43. Typically, there will be a small area of overlap 51 where opposite edges of the prismatic sheet material meet. Cylinder 47 has a length substantially equal to the internal length of light compartment 41. Mirror 53 is located inside cylinder 47, at the bottom of light compartment 41. As a result of the internal reflectance of the prismatic sheet material and the reflectance of mirror 53 and reflector 27, light from light source 30 is, to a large extent, reflected back into the chamber formed by cylinder 47. Light escapes from cylinder 47 due to minor imperfections in the prismatic sheet material or the angle of incidence of the light. The net result of this internal reflectance is that the light from light source 30 is distributed substantially uniformly across the inner surface of wall 43 and thus provides a highly controlled distribution of light throughout the light paths created by walls 43 of adjacent light compartments 41.

Although the light compartments 41 and prismatic sheet material 47 are shown in cylindrical form in the drawings, as taught in U.S. Pat. 4,260,220, equally effective light guides can be in the form of square or rectangular tubes or other convenient shapes. Thus, light compartments 41 can also be square, hexagonal, rectangular and the like in cross sectional shape. Likewise, although a cylindrical shape is preferred for tank 13, any convenient shape may be employed. It is preferable, although not essential, that the prismatic sheet material 47 be oriented such that the corrugations run in a longitudinal direction approximately parallel to a major component of the light rays.

As illustrated in FIG. 3, the photobioreactors of this invention are generally designed to accommodate a head space between the liquid algal culture surface 52 and lid 23. The head space allows for foaming, which often occurs in agitated biological culture media. To prevent the escape of light from light compartment 41 into the head space, a portion of light guide 41 which extends above liquid level 52 is advantageously lined with a mirror 55 or other reflective surface.

Tank 13 is fitted with gas inlet tube 15 which is provided with a pressurized gas (e.g., carbon dioxide or carbon dioxide-enriched air) for supporting the photosynthetic requirements of the algal culture. Tube 15 passes through the wall of tank 13 and is connected to one or more gas sparging tubes arranged along the bottom of tank 13. Gas bubbles rise through the liquid algal culture medium contained in tank 13 and the spent gases escape through exit tube 18, which is disposed in the wall of tank 13 above the surface level of the culture medium.

In a preferred embodiment, the gas sparging tubes can be configured such that the bubbling gas not only supports photosynthesis in the algal culture, but also assists in agitating the liquid culture medium. An example of such an embodiment is illustrated in FIGS. 1-3. In general, the interior of tank 13 is divided into two concentric compartments with fluid communication between such compartments at the top and bottom of the tank. This division is achieved by disposing septa 42 between adjacent light compartments in a concentric ring approximately midway between the center of tank 13 and the outer wall. Septa 42 may be solid plates which are fastened to the walls of adjacent light compartments and extend from a point somewhat above the bottom of tank 13 to a point somewhat below the surface level of the liquid culture medium. Alternatively, septa 42 may be jacketed plates which provide a means for cooling or heating the culture medium. Gas inlet tube 15 is connected to a sparging ring 50 which sits on the bottom of tank 13 that is in the shape of a concentric circle within the inner compartment formed by septa 42. Sparging ring 50 may be a perforated metal tube, a porous ceramic material or other aerating device, as is generally known in the art. As shown in FIG. 3, gas bubbles escape from sparging ring 50 and pass upwardly in the inner compartment formed by septa 42 until they escape from the surface of the liquid culture medium. The rising gas bubbles cause an upward movement of fluid in the inner compartment formed by septa 42. A downward movement of fluid in the outer compartment formed by septa 42 also results from the gas sparging. Thus, as depicted by the arrows in FIG. 3, the gas sparging causes a gentle circulation and mixing of the liquid algal culture contained in tank 13.

In the illustrated embodiment, a gas flow of about 0.1 volumes of gas per volume of culture medium per minute is sufficient to satisfy the photosynthetic requirements of the culture medium and provide a thorough mixing. If more vigorous mixing is desired, a circulating pump 79 powered by motor 80 may be used to agitate the culture medium. During this mode of operation, valve 82 is closed and valve 83 is opened, thus allowing recirculation of culture medium in tank 13. Of course, other types of agitators may also be employed.

It will be appreciated that the photobioreactors of this invention can be produced in widely varying sizes. A large number of light assemblies and light compartments may be grouped together to produce large scale photobioreactors. For simplicity, a photobioreactor employing six light assemblies and light compartments has been illustrated; however, in a typical industrial scale photobioreactor, one hundred or more light assemblies and light compartments might be employed. In a typical construction, each light compartment has a diameter of about six inches. The length of the light compartment will depend largely upon the power output of the light source. For example, a 250 watt bulb provides adequate lighting for a light compartment five feet in length. A 400 watt bulb provides adequate lighting for an eight-foot light compartment and a 1,000 watt bulb may be used to illuminate a twenty-foot light compartment. In general, the light compartments are spaced such that about 2.5 liters of liquid culture medium is accomodated for each linear foot of light compartment length. Thus, a photobioreactor containing 61 20-foot light compartments will have a volume of a about 3350 liters.

Operation

The operation of the photobioreactor depicted in FIGS. 1-4 is straightforward. Typically, prior to filling the photobioreactor with a biological culture medium, the interior of the photobioreactor is sanitized by exposing it to a sterilizing gas, a hypochlorite solution or the like. Following sanitization, water is introduced into tank 13 via a pressurized water line (not shown), valve 72 and pipe 70. Tank 13 is filled with water to a predetermined depth such that the surface of the culture medium will be below exit port 18. Nutrients and inocula are introduced into tank 13 through access port 75. Alternatively, lid 23 and plate 22 may be raised to provide access to the top of tank 13. After establishing the desired composition of the aqueous culture medium, lid 23, plate 22 and the accompanying structures are set into place. The pH and temperature of the medium may be monitored throughout the photobioreaction by means of temperature probe 76 and pH probe 77. The photobioreaction is initiated by supplying electrical power to light sources 30 and initiating sparging of an appropriate gas mixture via inlet tube 15. The progress of the photoreaction may be monitored with a calibrated density detector 81. Adjustments to the pH or the composition of the culture medium may be effected by introducing materials through access port 75 or by an automatic detection and feedback mechanism (not shown).

When the cells are ready to harvest, the light sources and sparging gas are turned off, valve 82 is opened and valve 83 is closed, thus permitting the culture medium to be expelled by pump 79 via pump 85 to a recovery operation.

Laboratory Scale Photobioreactor

Figure 5:
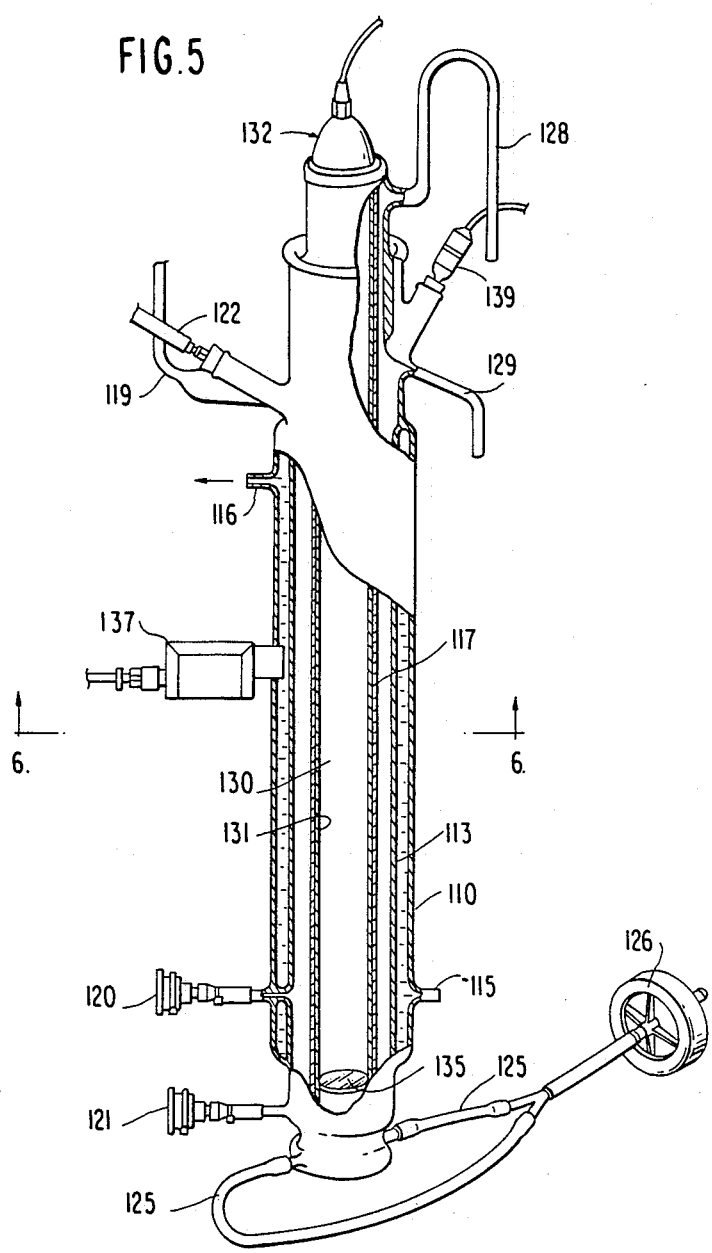
FIG. 5 is a perspective view in partial section of an alternative embodiment of a photobioreactor according to the present invention.
Figure 6:
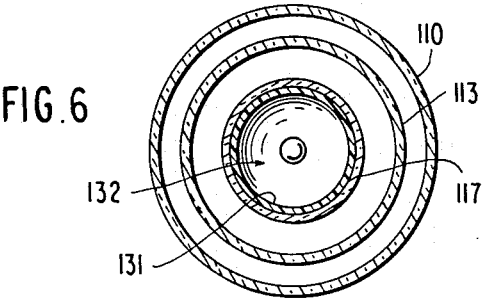
FIG. 6 is a cross-section of the photobioreactor shown in FIG. 5 taken along lines 6—6 of FIG. 5.

The foregoing discussion has focused on the construction of industrial scale or pilot plant size photobioreactors. The principles of the present invention are equally applicable to laboratory scale photobioreactors and the concerns about safety, and to a lesser extent, efficiencies, are equally applicable. A laboratory scale reactor in accordance with the present invention is illustrated in FIGS. 5 and 6. The reactor consists of concentric glass tubes which create cylindrical compartments for containing a light distribution means, a liquid algal cell culture, and cooling or heating fluid. Walls 110 and 113 define a water jacket to which cooling or heating water may be circulated via inlet port 115 and outlet port 116. Walls 113 and 117 define a concentric liquid algal culture chamber. This chamber may be accessed via medium inlet tube 119, septums 120 and 121 and inlet tube 122. Gas for supporting photosynthesis of the algae is introduced into the bottom of the algal culture chamber via tubes 125 and filter 126. Gas outlet tube 128 permits gas to escape from the algal culture medium chamber. Overflow tube 129 provides a means for operating the system in a continuous manner.

The progress of the reaction in the photobioreactor depicted in FIG. 5 may be monitored with calibrated density detector 137. The pH of the culture medium may be monitored by means of pH probe 139.

The interior of glass cylinder 117 forms light compartment 130. At the upper end of light compartment 130 is mounted lamp assembly 132 which includes a reflector and a high intensity lamp (not shown). The reflector directs the light down into light compartment 130. Disposed within light compartment 130 is a cylinder 131 of the reflective prismatic sheet material described above. At the bottom of light compartment 130 is mirror 135. Thus, the reflector of light assembly 132, the cylinder of prismatic sheet material 131, and mirror 135 cooperate to distribute light uniformly across the interior wall of cylinder 117 and thus provide a uniform source of light to the algal culture chamber formed by cylinders 117 and 113.

The invention has been described in connection with certain preferred embodiments; however, it will be appreciated that it is susceptible to various modifications, changes and adaptations, all of which are intended to be comprehended within the meaning and range of equivalants of the appended claims.

I claim:

1. A photobioreactor which comprises:

(a) a tank for containing a liquid microbial culture;
    (b) a high-intensity light source whose light is substantially entirely directed into a light compartment;
    (c) said light compartment having at least one transparent wall extending into said tank; and
    (d) said light compartment containing a tube of internally reflective prismatic sheet, said tube extending substantially from said light source to an end wall of said light compartment opposite said light source and said tube having transverse dimensions sufficient to substantially surround said light source, said tube further including a mirror at the end thereof opposite said light source oriented to reflect light back into said tube, wherein the light source, the tube and the mirror are arranged, so as to distribute light from said high-intensity light source substantially uniformly across the interior surface of the transparent wall of said light compartment.

2. The photobioreactor of claim 1, wherein said light compartment is substantially cylindrical in shape and is constructed of a transparent material.

3. The photobioreactor of claim 2, wherein said tube of prismatic sheet is oriented such that corrugations on the surface of such material are oriented substantially parallel t the longitudinal axis of said light compartment.

4. The photobioreactor of claim 2, wherein said tube of prismatic sheet is in the form of a hollow cylinder having a diameter substantially equal to the interior dimensions of said light compartment.

5. The photobioreactor of claim 1, wherein the light compartment has a rectangular cross sectional shape and the tube of prismatic sheet is either a cylindrical or rectangular tube.

6. The photobioreactor of claim 2,. wherein the dividers divide the tank into concentric cylindrical compartments.

7. The photobioreactor of claim 3, which comprises a plurality of high-intensity light sources and light compartments, each of said light compartments being disposed such that the longitudinal axes of adjacent light compartments are substantially parallel and the transparent walls of adjacent light compartments cooperate to form a light path of dimensions such that a photosynthesis-supporting amount of light is transmitted through the walls and substantially throughout said light path.

8. The photobioreactor of claim 7, wherein the light path formed by walls of adjacent light compartments ranges from 1.5 to about 50 centimeters.

9. The photobioreactor of claim 8, wherein the intensity of the light in the visible region of the spectrum which is distributed across the inner surface of said transparent wall ranges from 10 to 100 watts per square meter.

10. The photobioreactor of claim 9, wherein the intensity of the light distributed across the inner surface of said transparent wall ranges from 30 to 60 watts per square meter.

11. The photobioreactor of claim 7, wherein the light path formed by walls of adjacent light compartments ranges from 1.5 to about 3 centimeters.

12. The photobioreactor of claim 7, wherein the light path formed by walls of adjacent light compartments ranges from 30 to 50 centimeters.

* * * * *

UNITED STATES PATENT AND TRADEMARK OFFICE
CERTIFICATE OF CORRECTION

Page 1 of 2

PATENT NO. : 4,952,511

DATED : August 28, 1990

INVENTOR(S) : Radmer

It is certified that error appears in the above-identified patent and that said Letters Patent is hereby corrected as shown below:

Title page, col. 2, line 11, "Biotech Y Bioeng." should be --Biotech & Bioeng.--.

Col. 1, line 35, after "inexpensive" insert --,--.

Col. 2, line 21, after "employed" insert --.--;
line 58, after "29" insert --,--;
line 58, "488-4392" should be -- 482-492--;
line 60, "operate ions," should be --operations--.

UNITED STATES PATENT AND TRADEMARK OFFICE
CERTIFICATE OF CORRECTION

PATENT NO. : 4,952,511

DATED : August 28, 1990

INVENTOR(S) : Radmer

It is certified that error appears in the above-identified patent and that said Letters Patent is hereby corrected as shown below:

Col. 10, line 3, after "entirely" insert --collected and--;
line 6, delete "and";
line 12, after "surround" insert --the path of light from--;
line 20, after "partment" insert
--; and
(e) the interior of said tank containing dividers dividing said tank into adjacent compartments, said compartments being in fluid communication at the top and bottom of the tank, and said tank further comprising gas sparging means in at least one of said compartments such that the bubbling of gases from said sparging means causes circulation of a fluid from one compartment to another.--;

line 24, "2" should be --1--;
line 27, "t the" should be --to the--;
line 51, delete "about";
line 63, delete "about".

Signed and Sealed this

Twenty-fifth Day of May, 1993

Attest:

MICHAEL K. KIRK

Attesting Officer

Acting Commissioner of Patents and Trademarks